US008696688B2

(12) United States Patent
Stone

(10) Patent No.: US 8,696,688 B2
(45) Date of Patent: Apr. 15, 2014

(54) METHOD AND APPARATUS FOR PASSING A FLEXIBLE STRAND

(75) Inventor: Kevin T Stone, Warsaw, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 1580 days.

(21) Appl. No.: 11/346,540

(22) Filed: Feb. 2, 2006

(65) Prior Publication Data

US 2007/0179510 A1    Aug. 2, 2007

(51) Int. Cl.
*A61B 17/04*    (2006.01)

(52) U.S. Cl.
USPC ............................ 606/144; 606/148

(58) Field of Classification Search
USPC ........... 606/144–148, 139, 74, 103, 108, 205;
600/585; 140/93 R, 52–53, 123;
289/17; 604/156, 271, 117; 623/1.11;
112/169
See application file for complete search history.

(56) References Cited

U.S. PATENT DOCUMENTS

| | | | | |
|---|---|---|---|---|
| 3,835,854 A * | 9/1974 | Jewett | ........................ | 604/159 |
| 4,890,615 A * | 1/1990 | Caspari et al. | ................ | 606/146 |
| 4,923,461 A * | 5/1990 | Caspari et al. | ................ | 606/146 |
| 4,935,027 A * | 6/1990 | Yoon | ............................. | 606/146 |
| 4,957,498 A * | 9/1990 | Caspari et al. | ................ | 606/146 |
| 5,254,126 A * | 10/1993 | Filipi et al. | .................... | 606/146 |
| 5,290,310 A * | 3/1994 | Makower et al. | ............. | 606/213 |
| 5,318,541 A * | 6/1994 | Viera et al. | .................... | 604/159 |
| 5,346,498 A * | 9/1994 | Greelis et al. | ................. | 606/108 |
| 5,447,512 A * | 9/1995 | Wilson et al. | ................. | 606/139 |
| 5,643,292 A * | 7/1997 | Hart | .............................. | 606/144 |
| 5,690,645 A * | 11/1997 | Van Erp | ........................ | 606/108 |
| 5,746,753 A * | 5/1998 | Sullivan et al. | ............... | 606/147 |
| 5,755,728 A * | 5/1998 | Maki | ............................. | 606/145 |
| 5,766,186 A * | 6/1998 | Faraz et al. | .................... | 606/145 |
| 5,971,991 A * | 10/1999 | Sunderland | .................. | 606/108 |
| 6,022,360 A * | 2/2000 | Reimels et al. | ............... | 606/144 |
| 6,171,234 B1 * | 1/2001 | White et al. | .................... | 600/102 |
| 6,629,984 B1 * | 10/2003 | Chan | ............................. | 606/148 |
| 7,294,135 B2 * | 11/2007 | Stephens et al. | ............. | 606/108 |
| 7,591,268 B2 * | 9/2009 | Lowe et al. | .................... | 128/830 |
| 7,704,262 B2 * | 4/2010 | Bellafiore et al. | ............ | 606/144 |
| 8,221,305 B2 * | 7/2012 | Suzuki | .......................... | 600/106 |
| 8,425,465 B2 * | 4/2013 | Nagano et al. | ................ | 604/156 |
| 2003/0015203 A1 * | 1/2003 | Makower et al. | ............. | 128/831 |
| 2003/0153948 A1 | 8/2003 | Morrison et al. | | |
| 2005/0080476 A1 * | 4/2005 | Gunderson et al. | .......... | 623/1.11 |
| 2005/0165417 A1 * | 7/2005 | Sauer et al. | ................... | 606/144 |
| 2005/0245847 A1 * | 11/2005 | Schaeffer | ...................... | 600/585 |
| 2005/0283171 A1 * | 12/2005 | Bellafiore et al. | ............ | 606/144 |
| 2006/0025721 A1 * | 2/2006 | Duffy et al. | ............. | 604/164.12 |

OTHER PUBLICATIONS

"SpeedPass Suture Retrievers," copyright 2004 Arthrotek, Inc.

* cited by examiner

*Primary Examiner* — Corrine McDermott
*Assistant Examiner* — Mark Mashack
(74) *Attorney, Agent, or Firm* — Harness, Dickey

(57) ABSTRACT

An apparatus for passing a suture into a portion of the anatomy. The apparatus can include a handle and a suture advancement mechanism. The suture advancement mechanism can be disposed in the handle and adapted to advance a suture. The apparatus can also include a member coupled to the handle and in communication with the suture advancement mechanism to receive the suture. A cannula can be coupled to the member for receipt of the suture. The cannula can be operable to engage the anatomy. The suture advancement mechanism can contact the suture along a substantial distance of the suture to advance the suture into the member.

8 Claims, 4 Drawing Sheets

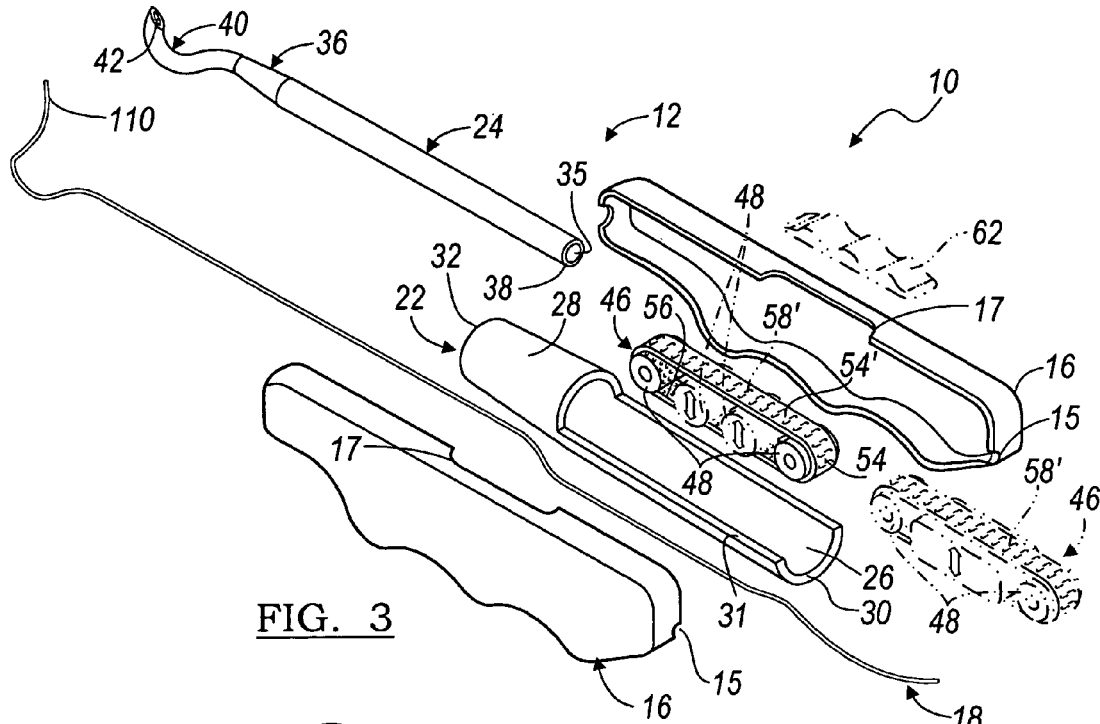
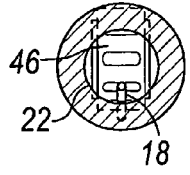
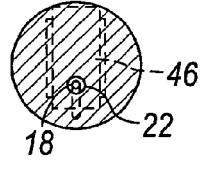
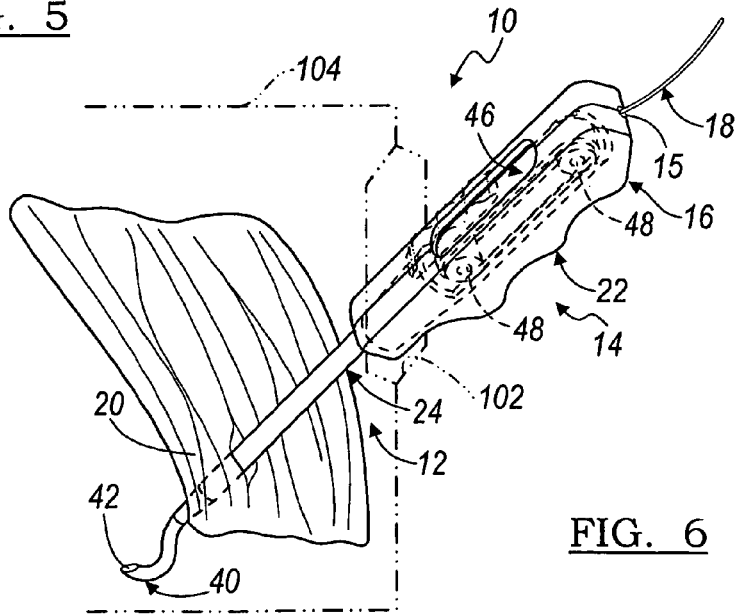

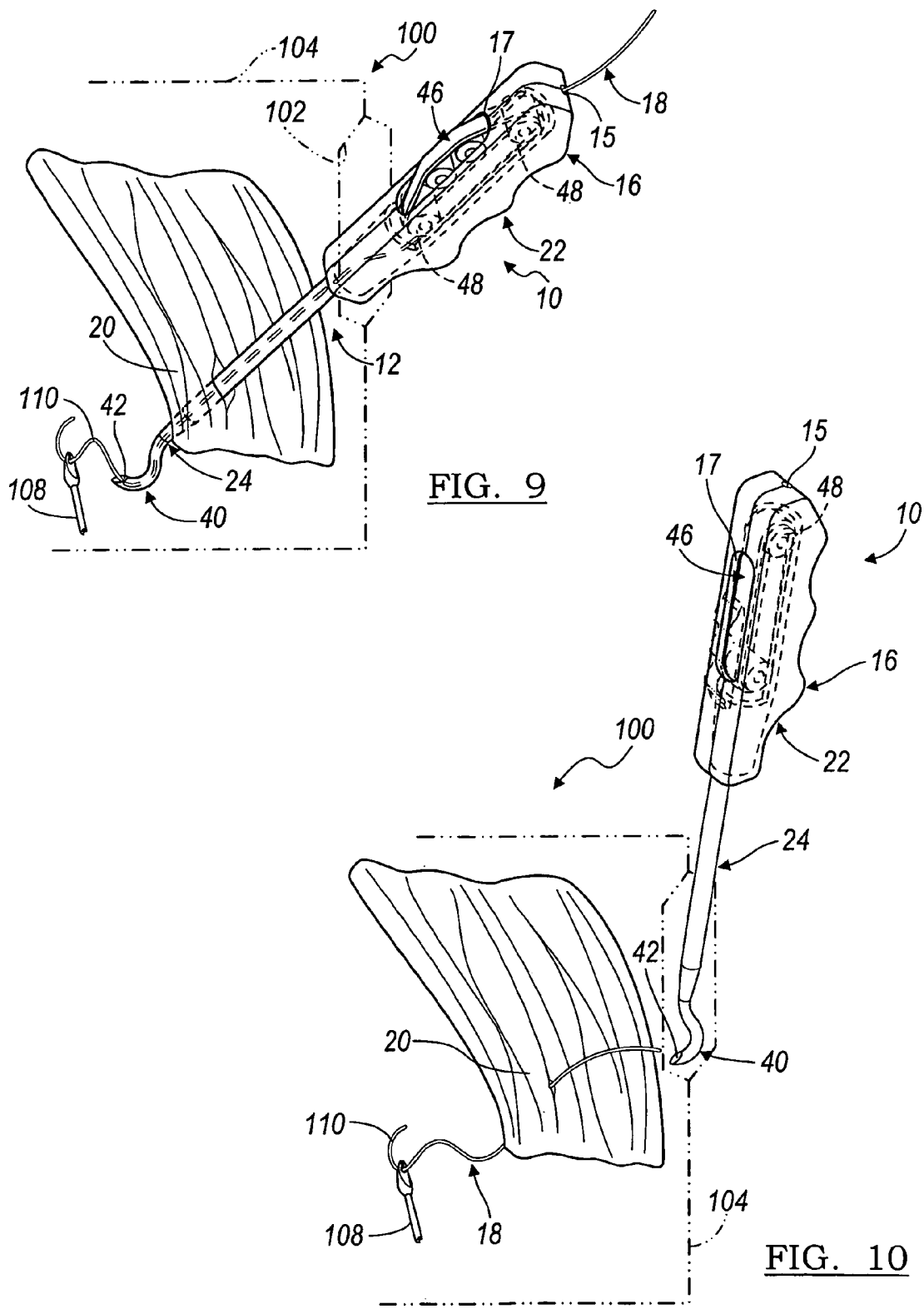

METHOD AND APPARATUS FOR PASSING A FLEXIBLE STRAND

FIELD

The present teachings relate generally to surgical instruments and procedures, and particularly to a method and apparatus for passing a suture.

BACKGROUND

One feature associated with the evolving field of medical technology is the continual effort to develop methods for repairing human tissue which require less disruption of the tissues and organs which surround an area requiring repair. In this regard, various forms of orthopedic surgery that once required that a large portion of a joint to be exposed during surgery can now be performed by making several small incisions. During such surgery, a fiber optic probe and various instruments are inserted into the incision to allow a surgeon to inspect and/or remove the damaged tissue without unduly disturbing the surrounding non-injured tissue. This type of surgery can be generally known as arthroscopic surgery.

While arthroscopic surgery, when available, can often be a desirable form of surgery due to its less intrusive nature, there are certain portions of the procedure that can be more difficult for the surgeon during such surgery. One difficulty which can be encountered includes suturing tissue during arthroscopic surgery. Suturing tissue during arthroscopic surgery can be somewhat difficult because a surgeon must manipulate the suturing instruments through a relatively small incision, not having clear and unobstructed view of the site, clean access to the sutures for tying, etc. Therefore, it may be desirable to provide a method and apparatus for passing a suture which can be effectively used in arthroscopic surgery.

SUMMARY

An apparatus for passing a flexible strand, such as suture, into a portion of the anatomy is disclosed. It will be understood that a suture can be any appropriate flexible strand. The apparatus can include a handle and a suture advancement mechanism. The suture advancement mechanism can be disposed in the handle and adapted to advance a suture. The apparatus can also include a member coupled to the handle and in communication with the suture advancement mechanism to receive the suture. A member with a throughbore therethrough which can also be referred to as a cannula can be coupled to the member for receipt of the suture. The cannula can be operable to engage the anatomy. The suture advancement mechanism can contact the suture along a selected distance of the suture to advance the suture into the member.

An apparatus for passing a suture into a portion of tissue is taught. The apparatus can include a handle and a suture passing mechanism, such as belt, disposed in the handle. The belt can be adapted to advance a suture. The apparatus can also include a member which can be coupled to the handle and in communication with the belt to receive the suture. The member can be configured to engage the anatomy. The belt can contact the suture along a selected distance of the suture to advance the suture into the member.

Also taught in various embodiments is a method for passing suture into a portion of the anatomy. The method can include positioning a member in the anatomy. The method can also include contacting a suture along a selected distance of the suture with a suture advancement mechanism to advance the suture into the member. The method can also include translating the suture advancement mechanism to advance the suture into the member, and providing a power source to translate the suture advancement mechanism to advance the suture.

A method for inserting a suture into a portion of tissue is taught. The method can include piercing the tissue with a member. The method can also include providing suture advancement mechanism, such as a belt, with a first surface and contacting a suture along a selected distance of the suture with the first surface of the belt. The method can also include providing a power source to engage the first surface of the belt, and translating the belt with the power source to advance the suture into the member. The method can further include removing the member from the tissue to leave the suture disposed in the tissue.

Further areas of applicability of the present teachings will become apparent from the detailed description provided hereinafter. It should be understood that the detailed description and various examples, while indicating various embodiments, are intended for purposes of illustration only and are not intended to limit the scope of the teachings.

BRIEF DESCRIPTION OF THE DRAWINGS

The present teachings will become more fully understood from the detailed description and the accompanying drawings, wherein:

FIG. 3 is a perspective exploded view of the apparatus for passing suture of FIG. 1;

FIG. 4 is a cross-sectional view of the apparatus for passing suture of FIG. 1, taken along line 4-4 of FIG. 2;

FIG. 5 is an alternative cross-sectional view of the apparatus for passing suture of FIG. 1, taken along line 4-4 of FIG. 2;

FIG. 6 is an environmental view of a procedure employed to begin the passing of suture into a selected portion of the anatomy according to various teachings;

FIG. 9 is an environmental view of an alternative handle for use with the apparatus for passing suture of FIG. 1; and FIG. 10 is an environmental view of a procedure employed to remove the apparatus from the suture after passing the suture into the portion of the anatomy according to various teachings.

DETAILED DESCRIPTION OF VARIOUS EMBODIMENTS

The following description of various embodiments is merely exemplary in nature and is in no way intended to limit the teachings, its application, or uses. Although the following description is related generally to an apparatus for passing suture that can be positioned in a portion of the anatomy, such as in a portion of tissue in an arthroscopic surgical procedure, it will be understood that the apparatus for passing suture, as described and claimed herein, can be used with any appropriate surgical procedure. Therefore, it will be understood that the following discussions are not intended to limit the scope of the appended claims.

Figure 1:
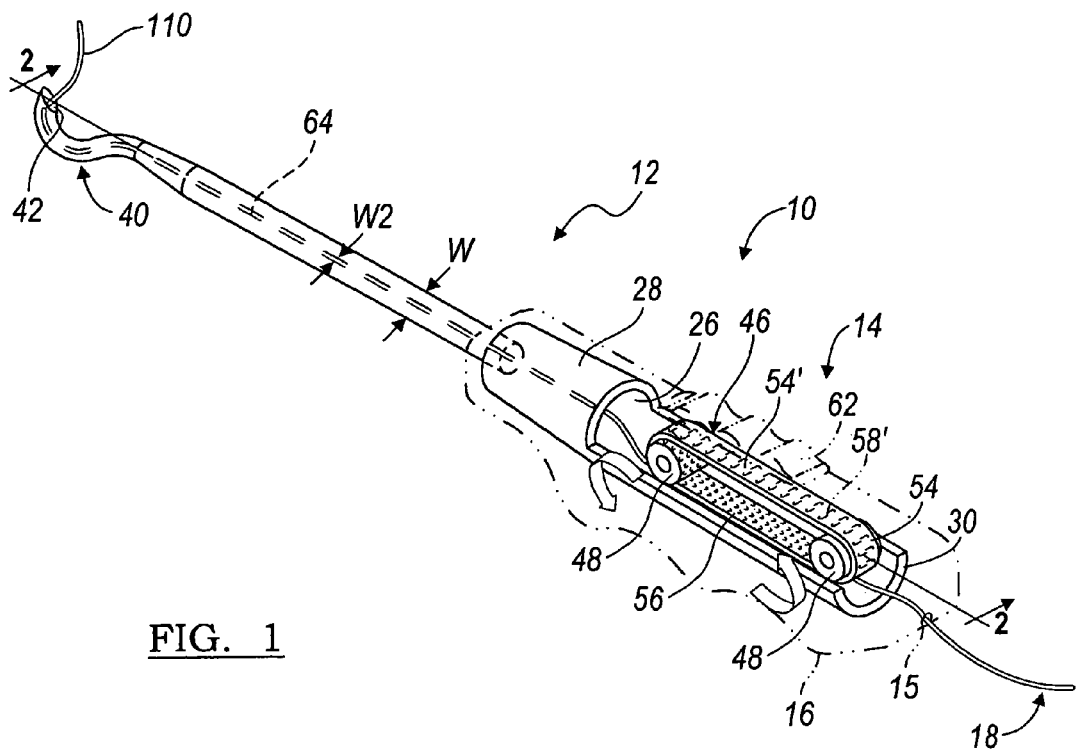
FIG. 1 is a detailed perspective view of an apparatus for passing suture according to various teachings.
Figure 7:
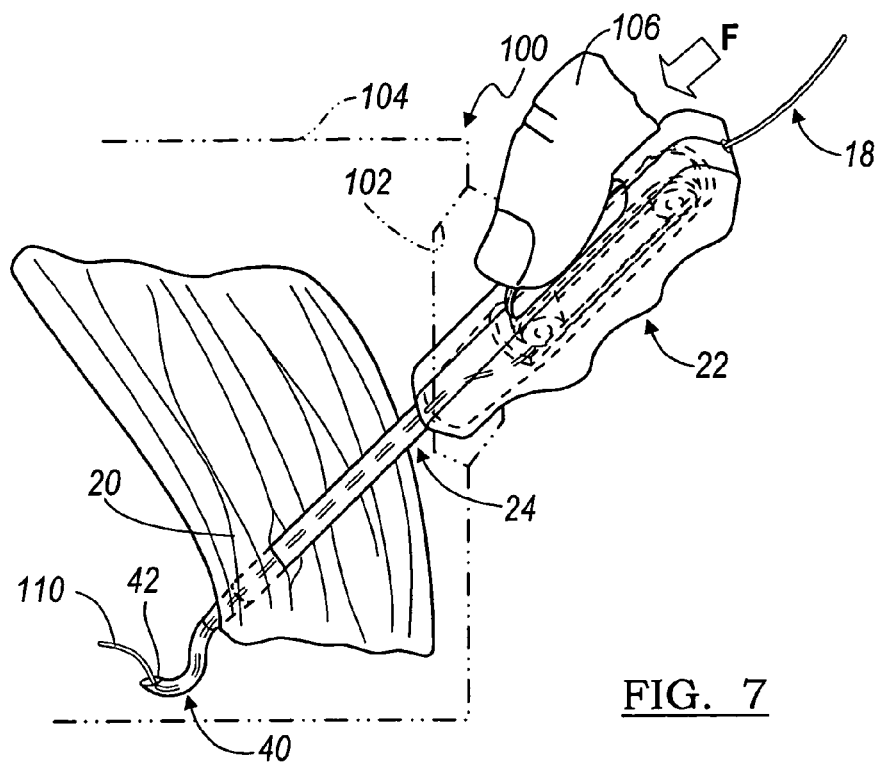
FIG. 7 is an environmental view of the apparatus passing suture into the portion of the anatomy.

As will be discussed in more detail herein, an apparatus for passing suture or suture passer assembly 10 is taught. With reference to FIG. 1, the suture passer assembly 10 can include a member 12 and a suture advancement mechanism 14 disposed in a housing or handle 16. The housing 16 can define an aperture 15 for receipt of flexible member, such as a suture 18 therein, and an opening 17 to enable the advancement of the suture 18 into the anatomy. Thus, the suture passer assembly 10 can be employed to pass the suture 18 through a portion of the anatomy, such as a section of tissue 20, as best shown in FIG. 7.

Figure 2:
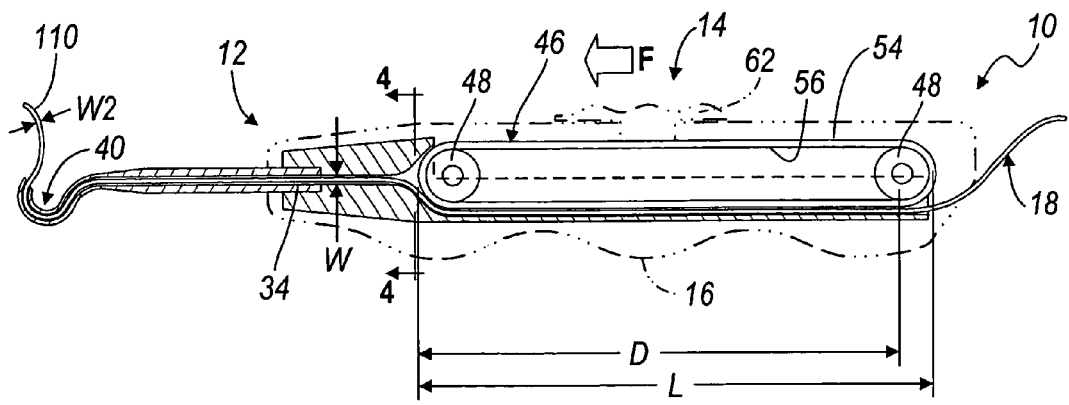
FIG. 2 is a detailed cross-sectional view of the apparatus for passing suture of FIG. 1, taken along line 2-2 of FIG. 1, illustrating a various teaching of the apparatus for passing a suture of FIG. 1.

With additional reference to FIGS. 2 and 3, the member 12 can include a suture receiving portion 22 and a tube defining a throughbore which can also be referred to as a cannula 24. The suture receiving portion 22 can define a hollow tubular shape with an interior surface 26 and an exterior surface 28. The suture receiving portion 22 may be composed of any appropriate material, such as a metal, metal alloy or a polymeric material. The interior surface 26 and exterior surface 28 can each have a selected texture, such as smooth. Generally, the suture receiving portion 22 can have a first end 30 and a second end 32. The first end 30 of the suture receiving portion 22 can receive the suture 18 and can include an opening 31 for receipt of the suture advancement mechanism 14 therein. The second end 32 can be covered and may have an opening 34. The opening 34 can be configured to engage the cannula 24 and to enable the suture 18 to pass therethrough. With reference to FIGS. 4 and 5, the opening 34 could either include a large diameter adjacent to the suture advancement mechanism 14 for receipt of the suture 18 (FIG. 4) or, in the alternative, can include a small diameter adjacent to the suture advancement mechanism 14 for receipt of the suture 18. With reference back to FIGS. 2 and 3, the suture receiving portion 22 can be the same as or included with the handle 16. The handle 16 and the suture receiving portion 22 can be one piece or multiple pieces.

The cannula 24 can be coupled to the suture receiving portion 22 through any appropriate technique such as molding or through a mechanical fastener (not shown). The cannula 24 can be composed of any appropriate material, such as a bio-compatible metallic material, such as titanium, titanium alloy, stainless steel, cobalt-chromium-molybedenum alloy, but any other bio-compatible material, such as a polymeric material, could be employed. The cannula 24 can define an interior channel 35 adapted to receive the suture 18 from the suture receiving portion 22.

The cannula 24 can have a width W which corresponds to a width W2 of the suture 18. The width W may either be slightly larger than the width W2 (as shown in FIG. 1) or may be substantially larger than the width W2 depending upon the suture 18 employed (as shown in FIG. 2) as will be discussed in greater detail below. The cannula 24 can also include a first end 36 and a second end 38. The first end 36 may form a tip 40. The tip 40 can be generally formed on the first end 36, but the tip 40 could also be coupled to the first end 36 through a secondary process, such as through a mechanical fastener or welding.

The tip 40 can be in any desired configuration, such as cylindrical, arcuate, pigtail or corkscrew (not specifically shown). Generally, the tip 40 has a sharp edge 42 for piercing the tissue 20 (FIG. 6). The second end 38 of the cannula 24 can include an opening 44 for receipt of the suture 18 therein. It will be understood, however, that although the cannula 24 is described as being separate from the suture receiving portion 22, it could be integrally formed with the suture receiving portion 22 if desired.

The suture advancement mechanism 14 can include a suture driving mechanism, such as a belt 46, which can translate about at least one or a plurality of members, such as axles, wheels or posts 48. Although a belt is described and used herein, it will be understood that the belt 46 could be any member capable of contacting the suture over a long length. The belt 46 can be disposed adjacent to the second end 32 of the suture receiving portion 22 of the member 12, or within the second end 32 of the suture receiving portion 22. The belt 46 can further include a first surface 54 and a second surface 56 adapted to translate about the posts 48.

The first surface 54 can be generally configured to contact the suture 18. The first surface 54 can contact the suture 18 over a selected distance D, which can be equivalent to a length L of the belt 46. It should be noted that the belt 46 can contact the suture 18 over the entire first surface 54, or the belt 46 can be flexible, and can contact the suture 18 on a flat portion of the belt 46 (not specifically shown). The distance D can be any appropriate length, such as about 1 mm to 50 mm. Since the belt 46 contacts the suture 18 over the distance D, the belt 46 can keep the suture 18 properly aligned with the cannula 24. The belt 46 contacts the suture 18 over a length to assist in aligning the suture 18 as it moves into the cannula 24. The suture 18, thus even if flexible, can be efficiently moved into the cannula.

The first surface 54 can also include at least one or a plurality of grooves 58 (as shown in phantom) to contact the suture 18, or the first surface 54 could be generally smooth. If the first surface 54 includes a plurality of grooves 58, the first surface 54 can contact the suture 18 at a plurality of discrete surfaces 54' defined by the grooves 58 to advance the suture 18. If the first surface 54 is generally smooth, the first surface 54 can contact the suture 18 along the selected distance D to advance the suture.

The first surface 54 can be contacted by a power source, such as a finger 106 (FIG. 7), motor, or other mechanism capable of translating the belt 46. The power source can contact a side of the belt 46 opposite the suture 18 to advance the suture 18. Generally, the power source can apply a force F in a first direction to translate the belt 46 in a generally clockwise direction to advance the suture 18 into the second end 32 of the member 12 (as best shown in FIG. 7). Alternatively, a slider 62 can be disposed in the opening 17 of the housing 16. The slider 62 could then be used to contact the first surface 54 of the belt 46 to advance the suture 18.

The second surface 56 of the belt 46 can also be generally smooth, but can include at least one or a plurality of grooves 58' as shown in phantom. The second surface 56 can be configured to translate about the posts 48. The posts 48 can be fixed to and/or retained in the housing 16 adjacent to the second end 32 of the suture receiving portion 22, or the posts 48 could be rotatably coupled to the housing 16 (as indicated by the rotational arrow in phantom in FIG. 1). Alternatively, the posts 48 and belt 46 could be molded on a carrier (not shown), and the carrier could be disposed in the housing 16 and in communication with the second end 32 of the suture receiving portion 22. One of the posts 48 can be disposed at the first end 50 of the belt 46 and a second one of the posts 48 can be disposed at the second end 52 of the belt 46, as shown, however, the posts 48 could be disposed at any location along the belt 46. Also, more than two of the posts 48 could be provided. In addition, additional posts 48 could be retained within the belt 46 but not coupled to the housing 16 to increase the force on the suture 18 to assist in advancing the suture 18 and in gripping the suture 18 during the advancement of the suture 18 (as shown in phantom in FIG. 3). Alternatively, as also shown in phantom in FIG. 3, posts 48' could be sized so as to "float" within the belt 46 to provide additional force on the suture 18 to assist in the advancement of the suture 18. Further, additional posts 48 could be rotatably coupled to and/or retained in the housing 16 to assist in raising the belt 46 out of the handle 16 to improve the ease of operation of the suture advancement mechanism 14 (as shown in FIG. 9). The posts 48, 48' may be composed of any suitable material, such as a polymeric material, but metals or metal alloys could also be employed.

The suture 18 can be any appropriate suture, such as a resorbable suture or a non-resorbable suture. Generally, the suture 18 can be a non-resorbable suture for use in arthroscopic surgical applications, such as a FiberWire suture or Tevdek suture from Arthrex, in Naples, Fla. If a resorbable or non-resorbable suture 18 is used, then the width W of the cannula 24 can be slightly larger than the width W2 of the suture 18 to prevent bunching of the suture 18 within the cannula 24 during the advancement of the suture 18 (FIG. 2). Alternatively, the suture 18 can be a reinforced suture 18 with a stiff end 64 (as shown in phantom in FIG. 1). If the suture 18 includes the stiff end 64, then the width W of the member 12 can be any desired size greater than the width W2 of the suture 18, as the stiff end 64 can prevent the suture 18 from bunching in the member 12 during the advancement of the suture 18 (FIG. 1).

With additional reference now to FIG. 6, the suture passer assembly 10 can be used to secure the suture 18 to tissue 20 in a portion of anatomy 100. In order to access the tissue 20, an incision 102 can be made into a selected portion of the skin 104 of a patient to provide access to the tissue 20. The size of the incision 102 can be any appropriate size, such as 1 cm to 50 cm, and can include 1 cm to 10 cm. In order to advance the suture 18 through the tissue 20, the suture passer assembly 10 can be inserted through the tissue 20 by using the tip 40 of the cannula 24 to pierce the tissue 20.

Figure 8:
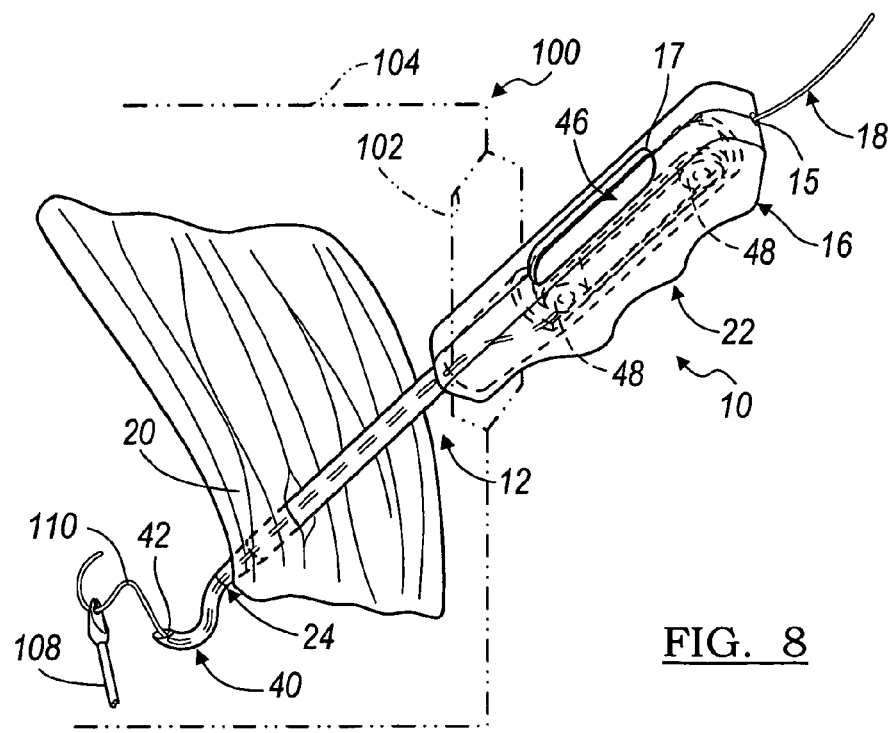
FIG. 8 is an environmental view of a procedure employed to secure the suture within the anatomy according to various teachings.

Once the tip 40 has pierced the tissue 20, the power source 60, such as a finger 106, can be applied to the belt 46 to begin translating the belt 46, as shown in FIG. 7. With reference to FIGS. 8 and 9, after the suture 18 extends from the tip 40, a grasper 108 can be inserted into the anatomy 100 through the incision 102, or any other incision. The grasper 108 can be of the type manufactured by Arthrotek, of Warsaw, Ind., and can generally include a pair of mating arms which can securely hold an end 110 of the suture 18 which extends beyond the cannula 24. Generally, the mating arms can be secured to a small amount of suture 18, and do not require a large amount of suture 18 in order to firmly hold onto the suture 18. After the grasper 108 is secured to the end 110 of the suture 18, the member 12 can be removed from the tissue 20, as best shown in FIG. 10. Generally, the operator can use the grasper 108 to hold the end 110 of the suture 18 taught as the member 12 is withdrawn from the tissue 20. It will be understood that only a small portion of the suture need be advanced to be grasped. By holding the end 110 of the suture 18 taught with the grasper 108, the suture 18 can pass through the member 12 and the belt 46, leaving the suture 18 within the tissue 20. With the suture 18 remaining disposed in the tissue 20, the operator can then use the suture 18 as necessary to secure the tissue 20 to the anatomy 100 (not specifically shown) according to various methods as is known in the art.

Thus, the suture passer assembly 10 can provide an efficient mechanism and method of inserting the suture 18 into a portion of the anatomy 100 without requiring a large incision 102. Further, the suture passer assembly 10 provides for smooth advancement of the suture 18 via use of the suture advancement mechanism 14. The use of the belt 46 also provides quick and easy advancement of the suture 18.

The description of these teachings is merely exemplary in nature and, thus, variations that do not depart from the gist of the teachings are intended to be within the scope of the teachings. Such variations are not to be regarded as a departure from the spirit and scope of the teachings.

What is claimed is:

1. An apparatus for passing a suture into a portion of an anatomy comprising:
    a graspable portion having an outer housing that defines an aperture at one end to receive the suture;
    a suture advancement mechanism disposed in the outer housing of the graspable portion adjacent to the aperture, the suture advancement mechanism adapted to advance the suture, the suture advancement mechanism including a belt having a first surface that contacts the suture, the belt including a first end spaced a distance apart from a second end, with a first post positioned at the first end and a second post positioned at the second end such that the first post is spaced a distance apart from the second post, the belt rotatable about the first post and the second post, a slider directly engaging the first surface of the belt to advance the suture;
    a member coupled to the graspable portion and in communication with the suture advancement mechanism to receive the suture, the member having an interior surface positioned and fixed opposite the first surface of the belt, with the suture advancement mechanism positioned such that the suture contacts the fixed interior surface of the member and the first surface of the belt;
    a cannula coupled to the member for receipt of the suture, at least a portion of the cannula operable to pass through a portion of the anatomy, the cannula defining an opening opposite the aperture that directs the suture into the anatomy; and
    wherein the suture advancement mechanism contacts the suture along a length of the suture to advance the suture into the member.

2. The apparatus of claim 1, wherein the member further comprises:
    a first end configured to be coupled to the cannula;
    a second end in communication with the suture advancement mechanism for receipt of the suture; and
    an open portion defined in the second end, the open portion operable to receive the suture advancement mechanism.

3. The apparatus of claim 2, wherein the belt has a second surface and the first post and the second post are configured to moveably engage the second surface of the belt, the first post and the second post assisting the belt to move the suture in a linear path.

4. The apparatus of claim 3, wherein the first post and the second post rotate about an axis on the member.

5. The apparatus of claim 1 wherein the first surface of the belt is smooth, grooved or combinations thereof.

6. The apparatus of claim 1, wherein the first surface of the belt is grooved and the belt engages the suture at a plurality of discrete surfaces along the length of the suture.

7. An apparatus for passing a suture into a portion of an anatomy comprising:
    a graspable portion having an outer housing that defines an opening and an aperture at an end for receipt of the suture;
    a suture advancement mechanism disposed in the outer housing of the graspable portion adjacent to the aperture and including a belt having a first surface that contacts the suture, a slider disposed in the opening and directly engaging the first surface of the belt to advance the suture;

a member coupled to the graspable portion having an open end that receives the suture advancement mechanism, and having an interior surface positioned and fixed opposite the first surface of the belt, the suture in contact with the fixed interior surface of the member and the first surface of the belt along a length of the suture;

a cannula coupled to the member for receipt of the suture, at least a portion of the cannula operable to pass through a portion of the anatomy and defining an opening opposite the aperture of the outer housing to direct the suture into the anatomy; and wherein the suture advancement mechanism contacts the suture along a length of the suture, which is equal to a length of the belt, to advance the suture from the aperture of the graspable portion to the opening in the cannula and the belt is supported by at least two posts that are separated by a distance.

8. An apparatus for passing a suture into a portion of an anatomy comprising:

an outer housing that defines a graspable portion, the outer housing defining an aperture at one end that receives the suture and defining an opening;

a suture advancement mechanism disposed in the outer housing adjacent to the opening, the suture advancement mechanism including a belt having a first surface that contacts the suture, with the belt supported by at least two posts that are spaced apart by a distance, a slider disposed in the opening and directly engaging the first surface of the belt to advance the suture;

a member disposed within the outer housing having a fixed interior surface, the suture advancement mechanism disposed in the outer housing between the opening of the outer housing and the fixed interior surface of the member so that the suture is in contact with the fixed interior surface of the member and the first surface of the belt;

a cannula coupled to the member for receipt of the suture, at least a portion of the cannula operable to pass through a portion of the anatomy and defining an opening opposite the aperture of the outer housing to direct the suture into the anatomy; and wherein the suture advancement mechanism contacts the suture along a length of the suture to advance the suture from the aperture of the outer housing to the opening in the cannula.

* * * * *